United States Patent [19]

Lioy et al.

[11] Patent Number: 5,373,748
[45] Date of Patent: Dec. 20, 1994

[54] WIPE TEMPLATE SAMPLER

[75] Inventors: Paul J. Lioy, Cranford; Clifford P. Weisel, Highland Park, both of N.J.

[73] Assignee: University of Medicine and Dentistry of New Jersey, Newark, N.J.

[21] Appl. No.: 101,260

[22] Filed: Aug. 3, 1993

Related U.S. Application Data

[63] Continuation-in-part of Ser. No. 949,382, Sep. 22, 1992, abandoned.

[51] Int. Cl.[5] .............................................. G01N 1/04
[52] U.S. Cl. ................................................... 73/864.71
[58] Field of Search ............... 73/864.71; 435/30, 292, 435/294, 295

[56] References Cited

U.S. PATENT DOCUMENTS

| | | |
|---|---|---|
| 3,074,276 | 1/1963 | Moos . |
| 3,091,967 | 6/1963 | Hurdlow et al. . |
| 3,362,141 | 1/1968 | Royster, Jr. et al. . |
| 3,554,039 | 1/1971 | Braun . |
| 3,572,128 | 3/1971 | Hemeon . |
| 3,897,688 | 8/1975 | Meserol et al. ................... 73/864.71 |
| 3,933,358 | 1/1976 | Hoer ...................................... 277/170 |
| 4,103,553 | 8/1978 | De Blasiis et al. . |
| 4,848,165 | 7/1989 | Bartilson et al. . |
| 4,848,167 | 7/1989 | Gordon et al. ................... 73/864.71 |

*Primary Examiner*—Robert Raevis
*Attorney, Agent, or Firm*—Klauber & Jackson

[57] ABSTRACT

A low cost, pressure insensitive, highly accurate portable house dust wipe template sampler having a dust pick-up element and a corresponding template having an aperture which exposes a testing surface of predetermined area. The dust pick-up element is comprised of a porous polyethylene "draindisc" filter removably mounted on an inert non-porous plastic body having a gripping handle. The polyethylene filter is sized to snugly fit across the sampling template of predetermined area. Three wipes within the template area by successive polyethylene filters provide a dust mass recovery efficiency/per given area of the template, in excess of 95%.

7 Claims, 1 Drawing Sheet

WIPE TEMPLATE SAMPLER

REFERENCE TO RELATED APPLICATION

The present application is a continuation-in-part application of U.S. Ser. No. 07/949,382, filed Sep. 22, 1992, now abandoned.

BACKGROUND OF THE INVENTION

This invention relates to wipe samplers for measuring pollution levels of various contaminants contained within household dust.

Wipe samplers for determination of pollutant levels have been very crude such as the use of simple tissue paper for dust pick-up and sampling. This procedure is of suspect accuracy in replicability.

Devices for more accurate measurements, particularly with respect to radiation and bacteria contamination have been developed but these devices have been overly complicated thereby restricting their widespread use in large scale pollution testing. Such devices have included spring loaded contact apparatuses to maintain uniformity in pickup. Even more complicated devices include wheeled mechanisms with tracking measurements, and the like, to permit measurement of contaminant pick-up per unit area or volume.

In the past, substantially all the wipe devices have utilized collection elements of known size (area or volume) for a determination of contamination/unit size. As a result, the collection elements generally defined the efficiency of the collection. Accordingly, uniformity in pick-up was critical thereby leading to highly complex and cumbersome devices. Examples of such devices include the one described in U.S. Pat. No. 3,074,276, disclosing the finger activated spring loaded pick-up which causes an adhesive film of predetermined size to pick up a radioactive smear sample.

U.S. Pat. No. 4,103,553 discloses an automated wheeled frame which carries the smear discs and which is spring biased for radioactive contamination measurements. The device has an odometer for measuring the distance travelled over the surface being examined.

U.S. Pat. No. 3,363,141, discloses sampling with a disc contained within an enclosed housing of defined volume in combination with compressed air to move contaminants in the desired direction.

U.S. Pat. Nos. 3,091,967; 3,554,039; and 4,848,165, disclose various mechanized wipe samplers, and U.S. Pat. No. 3,572,128, discloses a time operable wheel with a series of wipers to measure dust over a given period of time.

OBJECTS AND SUMMARY OF THE INVENTION

It is an object of the present invention to provide a simple, economical dust sampling device having a high degree of dust pick-up efficiency.

It is a further object of the present invention to provide said economical dust sampling device wherein accuracy is not dependent upon the dimensions of the pick up element or the manner of wipe sampling.

It is a still further object of the present invention to provide wipe sampling with a template, of defined area of sampling, to permit use of successive wiping elements for enhanced accuracy of pick-up measurements.

These and other objects, features and advantages of the present invention will become more evident from the following discussion and the drawings.

DETAILED DESCRIPTION OF THE INVENTION

Generally, the present invention comprises a low cost, pressure insensitive, highly accurate portable dust wipe sampler. The dust wipe sampler comprises a template element with an aperture for exposure of a surface area of pre-determined areal dimensions and wherein the aperture has at least two parallel sides. The dust wipe sampler further comprises a porous inert pick-up element removably mounted on a non-porous inert body preferably of plastic, having a gripping handle. The pick-up element is adapted to be utilized with the template element wherein the pick-up element is sized to snugly fit within the aperture of the template, across the surface area between the two parallel sides, into pick-up contact with the surface having the predetermined area. The template, also of a non-porous inert material such as plastic, is placed upon the surface to be sampled and the pick-up element is laterally moved within the aperture of the template to contact the entire exposed surface. Since the pick-up element is snugly sized to fit within the aperture to span the surface area between the two parallel sides, the entire exposed surface is contacted with a single lateral movement, with the sides of the template acting to guide such lateral movement. Depending upon the amount of dust in the exposed surface area, additional pick-up elements are utilized to ensure complete or substantially complete pick-up of layers of dust within the exposed template area. Generally, three pick up elements reproducibly provides a better than 95% efficiency of dust pick-up.

The template area is pre-determined and defines the unit area of pollutants and contamination and the pick-up element is sized to completely contact the template area with a lateral wiping. As a result, the dimensions of the pick-up elements and the uniformity of pick-up are substantially irrelevant for accurate collection of pollutants. As opposed to the prior art in which the pick-up element itself was determinative of the unit area being sampled, more than one pick-up element can be utilized to increase rather than to detrimentally decrease accuracy of pick-up parameters.

The template is preferably provided with a non skid base such as of an inert rubber to ensure that the template does not move during wipe sampling.

The pick-up element is of a high surface area porous material such as a porous plastic to maximize pick-up and particle retention. An ideal economical material is a porous polyethylene "draindisc" filter. The pick-up element is adhered to the plastic body by means of an adhesive or pressure sensitive adhesive strip. Alternatively, the entire device is sufficiently inexpensive that the pick-up element may be integral with the body, wherein the entire device may be sample tested as a unit and then cleaned for re-use.

DETAILED DESCRIPTION OF THE PREFERRED EMBODIMENT

Figure 1:
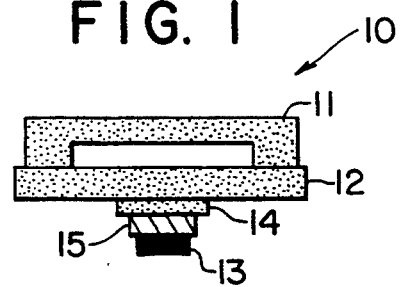
FIG. 1 is a side view of the wiping element of the present invention.
Figure 2:
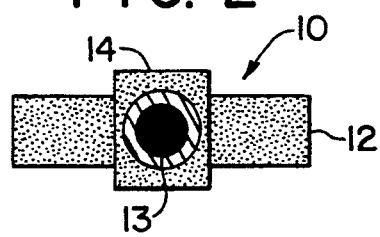
FIG. 2 is a bottom view thereof.
Figure 3:
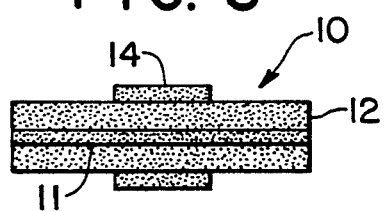
FIG. 3 is a top view thereof.
Figure 4:
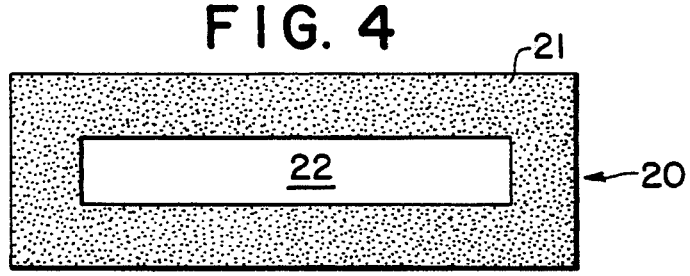
FIG. 4 is a top view of the template element of the present invention.
Figure 5:
FIG. 5 is a side view of the template element of FIG. 4.
Figure 6:
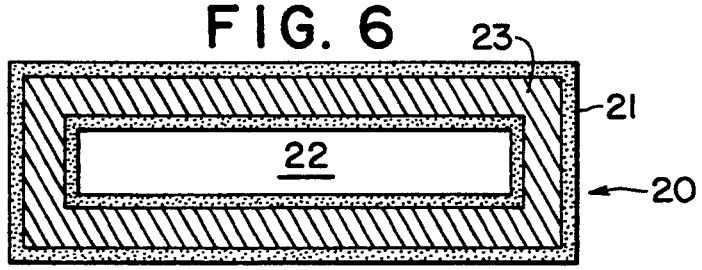
FIG. 6 is a bottom view of the template element of FIG. 4.

With specific reference to the drawings, in FIGS. 1–3, plastic body 12, of the wipe sampler 10 has an integral gripping handle 11 for ready wiping manipulation. A raised platform 14 on the side of the plastic body 12 opposite handle 11, provides a base for adherent support of a polyethylene "draindisc" filter 13 and a support base 15. Filter 13 is sized to snugly fit within a dimensionally defined aperture 22 of a template 20, which is shown in FIGS. 4–6.

In use, template 20 is placed upon a surface to be sampled. If the surface is contoured, template element 21 can be comprised of a sufficiently thin plastic whereby it is sufficiently flexible to follow the contours of the surface. Template base 23, of an inert rubber material, provides non-skid support for the template to prevent movement during wiping sampling.

A typical area defined by the template for dust sampling is a 50 cm$^2$ rectangular area, with a 40 mm short side and the typical draindisc filters are 37 mm in diameter which snugly fit therewithin. A simple conversion provides the pollution or contaminant levels of heavy metals such as lead and chromium in household dust in the appropriate $\mu g/m^2$ measurements. The use of three filters 13 within a single template area 22 has been found to consistently provide mass pick-up averaging in excess of 95%. Though the filters are shown as being round because of commercial availability, snugly fitted square or rectangular filters can provide even greater accuracy at the peripheral regions of the lateral wiping.

It is understood that the above description and drawings are illustrative of the present invention and details contained therein are not to be construed as limitations on the present invention. Changes in structure and materials and the like may be made without departing from the scope of the present invention as defined in the following claims.

What is claimed is:

1. A portable dust wipe sampler comprising:
   a non-porous, inert template element having an aperture formed therein for exposing a testing surface of pre-determined areal dimensions, wherein said template element comprises at least two parallel sides defining said aperture;
   a separate, non-porous, inert body element having an integral gripping handle; and
   a porous, inert pick-up element mounted on said separate, non-porous inert body element, wherein said pick-up element is dimensionally sized so as to snugly fit within said aperture of said template element between said two parallel sides, wherein said pick-up element, when placed within said aperture, comes into pick-up contact with said testing surface of pre-determined areal dimensions, and wherein a single lateral wiping motion by said body element enables said pick-up element to come into pickup contact with the entire area of said testing surface of pre-determined areal dimensions.

2. The portable dust wipe sampler as defined in claim 1, wherein said template element comprises a flexible template element so as to conform to contours in said testing surface.

3. The portable dust wipe sampler as defined in claim 2, wherein said template element and said body element are comprised of an inert non-porous plastic, and wherein said pick-up element is comprised of an inert porous plastic.

4. The portable dust wipe sampler as defined in claim 3, wherein said inert porous plastic comprises a porous polyethylene filter.

5. The portable dust wipe sampler as defined in claim 1, wherein said template element further comprises a non-skid element for non-skid contact with said testing surface.

6. The portable dust wipe sampler as defined in claim 1, wherein said pick-up element is removably mounted on said body element.

7. The portable dust wipe sampler as defined in claim 1, wherein said pick-up element is fixedly mounted on said body element.

* * * * *